United States Patent [19]

Finch

[11] 4,219,445

[45] Aug. 26, 1980

[54] METHANATION OF CARBON MONOXIDE OVER TUNGSTEN CARBIDE-CONTAINING ALUMINA CATALYST FOR METHANATION OF CARBON MONOXIDE

[75] Inventor: Jack N. Finch, Bartlesville, Okla.

[73] Assignee: Phillips Petroleum Company, Bartlesville, Okla.

[21] Appl. No.: 15,396

[22] Filed: Feb. 26, 1979

Related U.S. Application Data

[60] Division of Ser. No. 720,524, Sep. 7, 1976, Pat. No. 4,155,928, which is a continuation-in-part of Ser. No. 578,062, May 16, 1975, abandoned.

[51] Int. Cl.$^2$ .......................... B01J 21/04; B01J 27/22
[52] U.S. Cl. ................................. 252/443; 260/449 M
[58] Field of Search .................... 252/443; 260/449 M

[56] References Cited

U.S. PATENT DOCUMENTS

| | | | |
|---|---|---|---|
| 2,539,414 | 1/1951 | Frankenburg | 260/449 R |
| 2,755,228 | 7/1956 | Anhorn et al. | 196/50 |
| 3,770,658 | 11/1973 | Ozaki et al. | 252/443 |
| 3,787,468 | 1/1974 | Fleming et al. | 260/449 M |
| 3,790,410 | 2/1974 | Mund et al. | 252/443 X |
| 3,901,667 | 8/1975 | Herrmann | 260/449 M |
| 3,904,386 | 9/1975 | Graboski et al. | 423/656 X |

OTHER PUBLICATIONS

Schultz et al., Bureau of Mines, Report of Investigation No. 6974, (1967), pp. 1–6.
Mills et al., Catalyst Reviews, 8 (2), 159–210, 1973.

*Primary Examiner*—W. J. Shine

[57] ABSTRACT

A process of preparing methane-containing gas comprising contacting carbon monoxide and hydrogen in the presence of a catalyst containing tungsten carbide. Various tungsten carbide-containing alumina gel catalysts are also disclosed.

14 Claims, No Drawings

METHANATION OF CARBON MONOXIDE OVER TUNGSTEN CARBIDE-CONTAINING ALUMINA CATALYST FOR METHANATION OF CARBON MONOXIDE

This application is a divisional of application Ser. No. 720,524, filed Sept. 7, 1976 and now U.S. Pat. No. 4,155,928, which was in turn a continuation-in-part of application Ser. No. 578,062, filed May 16, 1975 and now abandoned.

This invention relates to the preparation of methane gas. In another aspect, this invention relates to the preparation of methane gas by the catalytic reaction of carbon monoxide and hydrogen. In another aspect, it relates to novel catalysts for the synthesis of methane from carbon monoxide and hydrogen.

Methanation catalysts and methanation processes are considered to be an important adjunct to preparing synthetic natural gas from coal or other carbon-containing materials. The gases obtained from coal gasification seem to have relatively low heating values and these values are often upgraded by converting the carbon monoxide produced to methane. As the availability of petroleum fuel sources decreases, such processes will most likely become increasingly important methods of providing our nation's energy needs.

A good review of the catalytic methanation of carbon monoxide is contained in the article "Catalytic Methanation" by G. Alex Mills and Fred W. Steffgen in *Catalysis Reviews*, Vol. 8, No. 2, pages 159–210 (1973). This article indicates that the methanation of carbon monoxide was first observed over a nickel catalyst. Thereafter, other metal catalysts were tested. It was found that copper, iron, platinum, and palladium did not form active catalysts. The work of Fischer, Tropsch, and Dilthey in the 1920's indicated that the decreasing order of methanation activity was Ru, Ir, Rh, Ni, Co, Os, Pt, Fe, Mo, Pd, and Ag. The article then goes on to indicate that the only metals now thought important for methanation are Ru, Ni, Co, Fe, and Mo. The article also points out, on page 198, that tungsten sulfide is an active methanation catalyst while a tungsten-alumina catalyst is not particularly effective. Page 199, of the article, also indicates that platinum metal catalysts are not particularly effective in methanation.

In accordance with the present invention, it has been surprisingly discovered that tungsten carbide-containing catalysts are suitable for the methanation of carbon monoxide.

It is therefore an object of this invention to provide a new process for the hydrogenation of carbon monoxide to produce methane. A further object of this invention is to provide new catalyst compositions to be employed in the methanation of carbon monoxide. These and other objects will be apparent from a study of this disclosure and the appended claims.

In accordance with the present invention carbon monoxide and hydrogen are reacted under methanation conditions in the presence of a catalyst comprising tungsten carbide-containing alumina gel produced by obtaining a substantial distribution of a catalytic amount of powdered tungsten carbide in the alumina hydrogel used in preparing the alumina gel. In a preferred embodiment the catalyst includes a promoting amount of at least one metal selected from the group consisting of ruthenium, rhodium, palladium, osmium, iridium, platinum and rhenium.

Generally any powdered tungsten carbide can be employed in preparing the above discussed catalyst. Preferably the average particle diameters of the tungsten carbide particles as determined by scanning electron microscopy is in the range of about 10 to about 100 micrometers. Both WC and $W_2C$ can be employed individually and mixtures of any ratio of the two are satisfactory. Generally, WC predominates in such mixture, however. The tungsten carbides can be formed by heating tungsten and carbon at high temperatures and recovering the product which is then crushed and sieved to obtain the powdered catalytic grade material. Of course, any conventional method can be employed for producing the powdered tungsten carbide employed in this invention.

The alumina hydrogel employed in preparing the inventive tungsten carbide-containing catalyst can be prepared by any known process. A substantial distribution of a catalytic amount of tungsten carbide in the alumina hydrogel can be achieved in any suitable manner. For example, the powdered tungsten carbide can be intimately mixed with freshly precipitated alumina hydrogel by stirring the hydrogel. Preferably, the alumina hydrogel is prepared in the presence of the tungsten carbide in such a fashion that there is substantial distribution of the tungsten carbide powder in the hydrogel. For example, the alumina hydrogel can be precipitated from a stirred solution containing the tungsten carbide. After the hydrogel is formed it is subjected to the conventional steps used in producing an alumina gel support, viz. washing to remove soluble impurities and drying to remove free water. The dried alumina gel is then preferably calcined in a nonoxidizing atmosphere. For example, the alumina gel can be calcined under flowing hydrogen. Generally the calcining is done by exposing the alumina gel to a temperature in the range of about 700° F. (370° C.) to about 1500° F. (815° C.) for about 1 to about 20 hours. Preferably, the calcination temperature is in the range of about 800° F. (425° C.) to about 1200° F. (650° C.) for about 2 to about 10 hours. Preferably, the resulting alumina gel catalyst is cooled to room temperature while still under a nonoxidizing atmosphere and then is ground or pulverized to give particles of about 16 to about 60 mesh size (U.S. Sieve Series).

Any amount of tungsten carbide can be employed in the alumina gel which provides a suitable catalytic effect. Generally, the weight ratio of tungsten carbide to alumina in the alumina gel is in the range of about 1/99 to about 80/20, preferably in the range of about 5/95 to about 60/40.

While any promoting amount of the above-mentioned promoting metals can be employed, generally the total amount of promoter metal employed is in the range of about 0.05 to about 5 weight percent, preferably about 0.1 to about 1 weight percent, of the weight of the promoted tungsten carbide-alumina catalyst.

The above-mentioned promoter metals can be incorporated into the catalyst using any techniques such as those conventionally employed for assuring the presence of catalytically active metals in an alumina gel. For example, a catalytically active form of promoter metal can be dispersed in the mixture used in preparing the hydrogel. Alternatively, suitable promoter metal compounds can be dispersed in the mixture used in preparing the hydrogel. The presence of the metals can also be assured by adding suitable metal compounds after the hydrogel has been formed, after the washing step, after the drying step, or even after the calcining step. Of course, if the metal compounds are added as a solution after the initial drying, the catalyst will again have to be dried. Solutions employed can be either suitable organic metal compounds or aqueous solutions of suitable inorganic metal compounds. Preferably, prior to use the alumina gel is calcined under a nonoxidizing atmosphere, as described above, at some time after the addition of the one or more promoter metals.

According to a preferred embodiment of the present invention the promoted tungsten carbide catalysts are prepared by impregnating portions of the ground tungsten carbide-alumina material with an aqueous solution of a platinum group, that is a Group VIII, metal compound sufficient to obtain the desired quantity of the metal. The resulting catalyst mixtures are then dried. All six platinum group metals, i.e., ruthenium, rhodium, palladium, osmium, iridium, and platinum can serve as promoters. Suitable compounds include the nitrates, haloacids, salts of the haloacids, complexes containing ammonia and the like. As indicated above while greater or lesser amounts can be employed, generally the amount of platinum group metal promoter is such that the total amount of promoter metal ranges from about 0.05 to about 5 weight percent based on the weight of the final composite, more preferably from about 0.1 to about 1 weight percent. (Final composite is used herein to denote the promoted catalyst after being dried of free water.)

As previously indicated a Group VIIB metal element, rhenium, can also serve as a promoter for the supported carbide catalysts. Thus the promoted tungsten carbide catalysts can be also prepared by impregnating portions of the ground carbide-alumina with a solution of a suitable rhenium compound. As with the Group VIII promoter, greater or lesser amounts can be employed but, generally, the quantity of the Group VIIB promoter metal is such that the total amount of promoter metal ranges from about 0.05 to about 5 weight percent based on the weight of the final composite, more preferably about 0.1 to about 1 weight percent. The promoter is composited with the supported carbide in the same manner as the Group VIII metal promoter previously described. Suitable rhenium compounds for this purpose include perrhenic acid, ammonium perrhenate, rhenium dioxide, rhenium pentachloride and the like.

The amount of tungsten carbide catalyst, alumina, Group VIII noble metal promoter, or Group VIIB promoter necessary for optimum conversion and selectivity can be determined by routine testing by one skilled in this art.

Reaction conditions usable in the process are analogous to those used with conventionally known methanation catalysts and will of course vary depending upon the exact catalyst used and the degree of conversion desired.

Generally the temperatures can vary from about 200° C. (392° F.) to about 600° C. (1112° F.), or more preferably from about 300° C. (572° F.) to about 550° C. (1022° F.). When a 50/50 tungsten carbide/alumina catalyst is employed, reactor temperatures of about 450° C. (842° F.) or higher are preferred. When the supported catalyst is additionally promoted with a small amount of a Periodic Group VIII metal such as platinum, it is possible to use reaction temperatures of only about 300° C. (572° F.) and yet achieve high conversion rates of 70-80 percent.

The pressure can range from 0 to 12,000 psig. Although the test data reported below were obtained only at atmospheric pressure in the practice of this invention, those skilled in the art recognize that generally thermodynamic consideration favor high reactor pressures.

The gaseous hourly space velocity (GHSV) of the feed gas in terms of volumes of gas per volume of catalysts per hour can range from about 200 to about 10,000. Preferably, the space velocity is in the range of about 600 to about 3,000 GHSV.

While the tungsten carbide-containing catalysts will tend to catalyze the methanation of any carbon monoxide/hydrogen stream, it has been found that as with many prior art methanation catalysts that it is preferred that the carbon monoxide and methane be employed in approximately stoichiometric proportions, viz. $H_2/CO = 3$, volumetric ratio.

The surprising activity of the inventive tungsten carbide-containing catalyst is illustrated by the following comparisons of catalyst activities.

EXAMPLES

A series of catalysts was prepared as follows for testing as catalysts for the conversion of hydrogen and carbon monoxide at a $H_2/CO$ volume ratio of about 3 to methane.

Catalyst A was prepared by impregnating a sample of catalytic grade alumina (flame hydrolyzed), previously water wet and calcined at 500° C. (932° F.) in air for one hour, ground and screened to 16-60 mesh particles with an amount of an aqueous solution of platinum diamminodinitrite which insured that the weight of platinum in the catalyst was equal to about 0.15 percent of the weight of the calcined alumina before addition of the platinum compound. It was dried at 125° C. (257° F.). This is a comparison or control catalyst.

Catalyst B was prepared by impregnating a sample of a catalytic grade alumina characterized by a specific surface area of 181 square meters per gram and apparent bulk density of 0.645 g/cc. with an amount of an aqueous solution of palladium nitrate which insured that the weight of palladium in the catalyst was equal to about 0.15 percent of the weight of the alumina before the addition of the palladium compound. The composite was dried at 125° C. (257° F.). This is a comparison catalyst.

Catalyst C was prepared by impregnating a sample of the catalytic grade alumina used in catalyst B with an amount of a solution of perrhenic acid which insured that the weight of rhenium in the catalyst was equal to about 0.15 percent of the weight of the alumina before the addition of the rhenium compound. The composite was dried at 125° C. (257° F.) and calcined two hours at 500° C. (932° F.) under flowing hydrogen and cooled under a hydrogen atmosphere. This is a comparison catalyst.

Catalyst D was prepared by impregnating a sample of the catalytic grade alumina used in catalyst B with an amount of an aqueous solution of sodium tungstate which insured that the weight of tungsten in the catalyst was equal to about 10 percent of the weight of the alumina before addition of the tungsten compound. The composite was dried at 125° C. (257° F.) and calcined under flowing CO for 5 hours at 550° C. (1022° F.). This is a comparison catalyst.

In preparing catalyst E powdered tungsten carbide, WC, commercially obtained was employed. It had an average particle size according to scanning electron microscopy of 31 micrometers. About 1.5 grams of the catalytic grade alumina used in catalyst B was mixed with about 4 grams of the tungsten carbide powder. This is a comparison catalyst.

Catalyst F was prepared dissolving about 36.7 grams of $Al(NO_3)\cdot 9H_2O$ in 100 cc of water and then slurrying therein 5 grams of the powdered tungsten carbide used in preparing catalyst E so that the final catalyst would consist of a 50/50 weight ratio of $WC/Al_2O_3$. The alumina hydrogel was formed by adding a solution containing concentrated ammonium hydroxide diluted with an equal quantity of water to the stirred mixture until a final pH of 8 was obtained. The purple gelatinous mass was filtered, washed with water, dried at 125° C. (257° F.), calcined under flowing hydrogen for two hours at 500° C. (932° F.) and cooled to room temperature under a hydrogen atmosphere. The final catalyst was ground to 16-60 mesh. A portion of the catalyst, analyzed by X-ray diffraction, showed patterns corresponding to the presence of WC plus $W_2C$. The ratio of each was not determined but it is believed that the $W_2C$ content was minor, i.e., below about 20 weight percent. This is an invention catalyst.

Three portions of catalyst F were individually impregnated with solutions of platinum diamminodinitrite, palladium nitrate and perrhenic acid, respectively. The amount of solution employed in each case was that necessary to insure that the weight of the promoter metal in the catalyst was equal to about 0.15 percent of the weight of that respective portion of catalyst F. Each composite was dried at 125° C. (257° F.). The resulting catalysts G, H, and I, respectively, are invention catalysts.

Preparatory to starting a run, each catalyst was charged individually to the reactor, heated under flowing hydrogen for two hours at 500° C. (932° F.) and cooled to 300° C. (572° F.) in flowing hydrogen. Sufficient carbon monoxide was introduced into the hydrogen stream to provide synthesis gas, nominally $H_2/CO = 3$, volumetric basis, and the run was started.

All the runs presented in the example were conducted in a continuous flow reactor operating at atmospheric pressure. Reactor effluents were analyzed by gas-liquid chromatography. Generally, carbon monoxide was continuously injected at about 13 cc/minute STP into hydrogen flowing at about 39 cc/minute STP to give synthesis gas in about stoichiometric proportions, i.e., $H_2/CO_3$ volume ratio of 3 or near 3. The supported catalysts were used in the form of 16-60 mesh particles.

With some of the catalysts a slug of carbon disulfide was introduced to test the resistance of the catalysts to sulfur poisoning. Presentation of conversion data poses problems since widely different $CH_4$ yields are possible, for a given CO conversion. As the $H_2/CO$ ratios are about 3, a formula proposed by the Institute of Gas Technology, Research Bulletin No. 31, page 10 is used to express the percent $H_2$-CO conversion to $CH_4$. This parameter which expresses conversion of $H_2$ and CO to $CH_4$ on an equal basis is defined in simplified form as follows:

$$\% \, CH_4 = 100 \left[ 4 \frac{(\text{moles dry product gas})}{(\text{moles dry feed})} \times (\text{mole fraction } CH_4 \text{ in dry product gas}) \right]$$

The results are presented in Tables I and II.

Table I

Tungsten Carbide Methanation Catalysts

| Run | 1 | | | 2 | | | 3 | | | 4 | | | 5 | | |
|---|---|---|---|---|---|---|---|---|---|---|---|---|---|---|---|
| Catalyst | A $Pt \cdot Al_2O_3$ (Control) | | | B $Pd \cdot Al_2O_3$ (Control) | | | C $Re \cdot Al_2O_3$ (Control) | | | D $WO_3 \cdot Al_2O_3$ (Control) | | | E $WO \cdot Al_2O_3$ | | |
| Time Hrs. | Temp. °C. | Feed GHSV | $CH_4$ % | Temp. °C. | Feed GHSV | $CH_4$ % | Temp. °C. | Feed GHSV | $CH_4$ % | Temp. °C. | Feed GHSV | $CH_4$ % | Temp. °C. | Feed GHSV | $CH_4$ % |
| 0.5 | 300 | 682 | 0 | 300 | 979 | 2.74 | 300 | 939 | 0 | 450 | 1039 | 0 | 300 | 2958 | 0.290 |
| 1.0 | ** | 682 | ** | ** | 979 | ** | ** | 939 | ** | 500 | 1089 | 0 | ** | 2958 | ** |
| 1.5 | ** | 682 | ** | 350 | 979 | 1.76 | 350 | 939 | 0 | 550 | 1089 | 0 | 350 | 2958 | 0.832 |
| 2.0 | 350 | 682 | 0.760 | 400 | 979 | 6.74 | 400 | 939 | 0.458 | | | | 400 | 2958 | 2.27 |
| 2.5 | 400 | 682 | 2.63 | 450 | 979 | 19.5 | 450 | 939 | 1.59 | | | | 450 | 2958 | 3.97 |
| 3.0 | 450 | 682 | 8.55 | 500 | 979 | 44.5 | 500 | 939 | 3.84 | | | | 500 | 2958 | 11.5 |
| 3.5 | 500 | 682 | 23.8 | 550 | 979 | 46.2 | 550 | 939 | 13.7 | | | | 500 | 2958 | 16.7 |
| 4.0 | 550 | 682 | 43.9 | 550* | 979 | 2.34 | 550* | 939 | 0.740 | | | | | | |
| $H_2/CO$ Volume Ratio | 3.1 | | | 3.0 | | | 3.0 | | | 3.2 | | | 2.7 | | |
| Remarks | 2.5 g. cat. | | | 2.5 g. cat. | | | 2.5 g. cat. | | | 2.5 g. cat. | | | 4 g. WC + 1.5 g. of 30-60 mesh $Al_2O_3$ Apparent bulk density of WC powder is 3.5 g/cc. | | |

*Introduced a 10 microliter slug of $CS_2$ between 3.5 and 4.0 hours
**No determination made in this time period.

Table II

Tungsten Carbide Methanation Catalysts

| Run | 6 | | | 7 | | | 8 | | | 9 | | |
|---|---|---|---|---|---|---|---|---|---|---|---|---|
| Catalyst | F $WC \cdot Al_2O_3$ | | | G $Pt \cdot WC \cdot Al_2O_3$ | | | H $Pd \cdot WC \cdot Al_2O_3$ | | | I $Re \cdot WC \cdot Al_2O_3$ | | |
| Time Hrs. | Temp. °C. | Feed GHSV | $CH_4$ % | Temp. °C. | Feed GHSV | $CH_4$ % | Temp. °C. | Feed GHSV | $CH_4$ % | Temp. °C. | Feed GHSV | $CH_4$ % |
| 0.5 | 300 | 1030 | 10.1 | 300 | 1338 | 70.9 | 300 | 1262 | 12.5 | 300 | 1235 | 75.7 |

Table II-continued

| | Tungsten Carbide Methanation Catalysts | | | | | | | | | | | |
|---|---|---|---|---|---|---|---|---|---|---|---|---|
| Run | 6 | | | 7 | | | 8 | | | 9 | | |
| Catalyst | F | | | G | | | H | | | I | | |
| | WC . Al$_2$O$_3$ | | | Pt . WC . Al$_2$O$_3$ | | | Pd . WC . Al$_2$O$_3$ | | | Re . WC . Al$_2$O$_3$ | | |
| Time Hrs. | Temp. °C. | Feed GHSV | CH$_4$ % | Temp. °C. | Feed GHSV | CH$_4$ % | Temp. °C. | Feed GHSV | CH$_4$ % | Temp. °C. | Feed GHSV | CH$_4$ % |
| 1.0 | ** | 1030 | ** | 350 | 1338 | 77.7 | ** | 1262 | ** | ** | 1235 | ** |
| 1.5 | 350 | 1030 | 5.04 | 400 | 1338 | 79.2 | 350 | 1262 | 9.78 | 350 | 1235 | 12.5 |
| 2.0 | 400 | 1030 | 2.33 | 450 | 1338 | systems failure | 400 | 1262 | 8.03 | 400 | 1235 | 9.88 |
| 2.5 | 450 | 1030 | 19.4 | 500 | 1338 | systems failure | 450 | 1262 | 45.4 | 450 | 1235 | 25.1 |
| 3.0 | 500 | 1030 | 49.4 | 550 | 1338 | 64.3 | 500 | 1262 | 62.8 | 500 | 1235 | 59.8 |
| 3.5 | 550 | 1030 | 57.8 | | | | 550 | 1262 | 64.4 | 550 | 1235 | 50.6 |
| 4.0 | 550 | 1030 | 65.5 | | | | 550* | 1262 | 45.1 | 550* | 1235 | 36.8 |
| 4.5 | 550 | 1030 | 65.9 | | | | 550* | 1262 | 1.74 | 550* | 1235 | 2.02 |
| H$_2$/CO Volume Ratio | 3.0 | | | 3.0 | | | 2.9 | | | 3.0 | | |
| Remarks | 2.5 g. cat. | | | 2.5 g. cat. | | | 2.5 g. cat. | | | 2.5 g. cat. | | |

**No determination made in this time period.
*Introduced a 10 microliter slug of CS$_2$ between 3.5 and 4.0 hours and between 4.0 and 4.5 hours.

Runs 1, 3, and 4 are in agreement with the teachings of the prior art contained in the above-mentioned *Catalysis Reviews* article. The tungsten-alumina catalyst, catalyst D, was quite inactive. An X-ray analysis was made on the catalyst D after use in Run 4. There was no indication that tungsten carbide was present. Catalyst A, platinum-alumina, and catalyst C, rhenium-alumina, were inactive until high temperatures were employed. The palladium-alumina catalyst, catalyst B, employed in Run 2 was slightly more active than the platinum-alumina catalyst.

Run 5 demonstrates that catalyst E, the admixture of tungsten carbide and alumina, was more active than catalyst D, the tungsten-alumina catalyst. If a feed rate more comparable to that used in Run 4 were used in Run 5 one would expect the production of methane to have been even greater since the conversion is generally inversely related to space velocity.

Although Runs 5 and 6 are not directly comparable due to the fact that different space velocities were employed, Run 6 is considered to indicate that catalyst F, tungsten carbide in alumina gel, is a more active methanation catalyst than catalyst E, the admixture of tungsten carbide and alumina. It is significant to note that catalyst E contained much more tungsten carbide than catalyst F. Assuming that conversion to methane is directly related to the amount of tungsten carbide present, if tungsten carbide were equally effective in either catalyst E or F one would have expected the methane production of Runs 5 and 6 to be more similar. The higher space velocity of Run 5 would be countered by the catalyst employed in Run 5 had higher concentration of tungsten carbide than the catalyst employed in Run 6.

Run 7 shows the effect of promoting catalyst F with platinum. Note, that substantially higher production of methane at lower temperature is obtained with the platinum promoter. The results obtained with catalyst A in Run 1 provided no indication that such a substantial improvement in methane production would result from the employment of platinum in combination with the tungsten carbide in alumina gel.

Run 8 shows the effect of promoting catalyst F with palladium. The methanation activity of catalyst H was greater than that of catalyst B, Pd.Al$_2$O$_3$, or catalyst F, tungsten carbide in alumina gel. At 450° C. or higher a synergistic effect is clearly demonstrated. The run does, however, clearly demonstrate that an advantage is obtained by promoting catalyst F with palladium. Run 8 also causes one to appreciate even more how unusual the activity of catalyst G was. Referring back to Runs 1 and 2 it will be noted that Pd.Al$_2$O$_3$ was more active than Pt.Al$_2$O$_3$, but, when tungsten carbide in alumina gel was promoted with palladium the resulting catalyst was less active than tungsten carbide in alumina gel promoted with platinum. (Compare Runs 7 and 8.)

Run 9 shows the effect of promoting catalyst F with rhenium. The rhenium enhanced the methanation activity of catalyst F at all temperatures except 550° C. The cause for the extreme drop in methane production between 1.5 and 2 hours on stream was not known.

In view of this unusual drop in methanation activity, catalyst J was prepared. The preparation of catalyst J involved preparing a catalyst of tungsten carbide in alumina gel in the same way as in the preparation of catalyst F and then adding the rhenium in the same manner as in the preparation of catalyst I. Catalyst J was then evaluated in the same fashion that the other previously discussed catalysts were evaluated. The results are summarized below in Table III.

Table III

| | Run 10 - Evaluation of Catalyst J | | |
|---|---|---|---|
| Time, Hrs. | Temp., °C. | Feed, GHSV | CH$_4$, % |
| 0.5 | 300 | 1297 | Systems Failure |
| 1.5 | 350 | 1297 | 79.7 |
| 2.0 | 400 | 1297 | 79.5 |
| 2.5 | 450 | 1297 | 77.0 |
| 3.0 | 500 | 1297 | 70.7 |
| 3.5 | 550 | 1297 | 64.0 |
| 4.0 | 550* | 1297 | 63.3 |
| 4.5 | 550* | 1297 | 21.6 |
| 5.0 | 550* | 1297 | 1.65 |

*10 microliter slugs of CS$_2$ were introduced between 3.5 and 4 hours, 4 and 4.5 hours, and 4.5 and 5 hours.

The determination of the amount of methane production at 0.5 hours was not possible due to a malfunction in the analysis equipment. The other analyses, however, clearly show that rhenium does activate the methanation activity of a catalyst of tungsten carbide in an alumina gel. There was no drop in activity of catalyst J comparable to that observed with catalyst I. Evidently, catalyst I was subjected to partial poisoning from some unknown source during the evaluation reported in Table II. A comparison of the effects of catalysts C, F, and J suggests that at certain temperatures ranging from about 300° to about 500° C. the rhenium has a synergistic effect upon a catalyst of tungsten carbide in an alumina gel.

In view of the observed effect of catalysts of tungsten carbide in alumina gel, a series of catalysts were prepared using a different technique for providing the presence of tungsten carbide in a catalyst support material.

Catalyst K was prepared by impregnating a sample of the catalytic grade alumina used in catalyst B with an aqueous solution of sodium tungstate sufficient to give 10 weight percent W (12.6 weight percent $WO_3$) based on the weight of the alumina before addition of the tungsten compound. The composite was dried at 125° C. (257° F.) and thereafter calcined in the presence of flowing carbon monoxide for about 4 hours at 800° C.

Catalyst L was prepared by heating a commercially used 16–60 mesh tungsten oxide-silica dioxide catalyst, denoted as R-2324 by Phillips Petroleum Company, in the presence of flowing carbon monoxide for about 4 hours at 800° C.

Catalyst M was prepared by heating the same 16–60 mesh tungsten oxide-silica dioxide catalyst for about 4 hours at 800° C. in the presence of flowing synthesis gas composed of about 50.9 volume percent hydrogen, 18.7 volume percent carbon monoxide, 27 volume percent methane, 3.26 volume percent ethane, and 0.14 volume percent nitrogen.

Catalysts K, L, and M were evaluated for methanation activity. The results are summarized in Table IV.

Table IV

| | Tungsten Carbide Containing Catalysts | | | | | | | | |
|---|---|---|---|---|---|---|---|---|---|
| Run | 11 | | | 12 | | | 13 | | |
| Catalyst | K | | | L | | | M | | |
| Time, Hrs. | Temp., °C. | Feed, GHSV | $CH_4$, % | Temp., °C. | Feed, GHSV | $CH_4$, % | Temp., °C. | Feed, GHSV | $CH_4$, % |
| 0.5 | 450 | 1080 | 0 | 450 | 506 | 0.35 | 450 | 488 | 0 |
| 1.0 | 500 | 1080 | 0 | 500 | 506 | 0 | 500 | 488 | 0 |
| 1.5 | 550 | 1080 | 0 | ** | ** | ** | 550 | 488 | 0 |
| 2.0 | 600 | 1080 | 0 | 550 | 506 | 2.2 | 600 | 488 | 0 |
| 3.0 | 700 | 1080 | 1.39 | ** | ** | ** | ** | ** | ** |
| 3.5 | ** | ** | ** | 600 | 506 | 3.7 | 700 | 488 | 0.86 |
| 4.0 | 800 | 1080 | 1.19 | ** | ** | ** | | | |
| 4.5 | 550 | 1080 | 0.47 | 750 | 506 | 5.29 | | | |

**No determination made in this time period.

After the evaluation of methanation activity an X-ray analysis was made on catalysts K, L, and M. The presence of tungsten carbide was indicated in each catalyst. The pattern for catalyst M was weak which suggests that the concentration of tungsten carbide was very low. The formation of tungsten carbide in these catalysts can be contrasted with the absence of tungsten carbide production during the preparation of catalyst D. Table IV demonstrates that the introduction of WC in the manner used in preparing catalysts K, L, and M did not result in significantly better methanation activity than that of ineffective catalyst D.

It is to be understood that the foregoing disclosure and examples are given only as an illustration and example to enable those skilled in the art to understand and practice the invention which involves the employment of tungsten carbide-containing catalysts in the methanation of carbon monoxide. Illustrative details disclosed in the foregoing are not to be construed as limitations on the invention. Obvious modifications and variations will be within the scope of the following claims.

What is claimed is:

1. A tungsten carbide-containing alumina catalyst produced by mixing powdered tungsten carbide in an alumina hydrogel to obtain a substantial distribution of said tungsten carbide in said hydrogel, washing the hydrogel with water to remove soluble impurities, drying the hydrogel to remove free water, and then calcining the dried hydrogel under a nonoxidizing atmosphere, wherein the amounts of alumina and tungsten carbide are such that the resulting catalyst will catalyze the conversion of carbon monoxide and hydrogen to methane.

2. A catalyst according to claim 1 wherein the weight ratio of tungsten carbide to alumina is in the range of about 1/99 to about 80/20.

3. A catalyst according to claim 2 wherein the average particle diameter of the particles of said powdered tungsten carbide is in the range of about 10 to about 100 micrometers.

4. A catalyst according to claim 3 which is promoted with at least one promoter metal selected from the group consisting of ruthenium, rhodium, palladium, osmium, iridium, platinum, and rhenium and the total amount of said promoter metal is in the range of about 0.05 to about 5 weight percent, based on the weight of the promoted dried tungsten carbide-containing alumina.

5. A catalyst according to claim 4 wherein said promoter metal is platinum.

6. A catalyst according to claim 4 wherein said promoter metal is palladium.

7. A catalyst according to claim 4 wherein said promoter metal is rhenium.

8. A catalyst according to claim 4 wherein said catalyst is prepared by slurrying powdered tungsten carbide with an aqueous solution of aluminum nitrate, forming the alumina hydrogel while stirring said slurry by adding a sufficient amount of ammonium hydroxide to said slurry to give a pH of about 8, filtering the hydrogel, washing the hydrogel, drying the hydrogel at about 125° C., calcining the dried hydrogel under flowing hydrogen at a temperature of about 500° C. for about 2 hours, then grinding the calcined product to yield particles of about 16 to about 60 mesh.

9. A catalyst according to claim 8 wherein said promoter metal is added to the ground tungsten carbide-containing alumina in the form of an aqueous solution of a suitable inorganic compound of said promoter metal, then the treated alumina is dried, and then the dried alumina is calcined for about two hours at about 500° C. under flowing hydrogen.

10. A catalyst according to claim 9 prepared by impregnating the ground tungsten carbide-containing alumina with a sufficient amount of platinum diaminodinitrite to provide about 0.15 weight percent platinum based on the weight of the unpromoted ground tungsten carbide-containing alumina.

11. A catalyst according to claim 9 prepared by impregnating the ground tungsten carbide-containing alumina with a sufficient amount of palladium nitrate to provide about 0.15 weight percent palladium based on the weight of the unpromoted ground tungsten carbide-containing alumina.

12. A catalyst according to claim 9 prepared by impregnating the ground tungsten carbide-containing alumina with a sufficient amount of perrhenic acid to provide about 0.15 weight percent rhenium based on the weight of the unpromoted ground tungsten carbide-containing alumina.

13. A catalyst according to claim 9 prepared by impregnating the ground tungsten carbide-containing alumina with a sufficient amount of perrhenic acid to provide about 0.15 weight percent rhenium based on the weight of the unpromoted ground tungsten carbide-containing alumina.

14. A catalyst according to claim 3 wherein said catalyst is prepared by slurrying powdered tungsten carbide with an aqueous solution of aluminum nitrate, forming the alumina hydrogel while stirring said slurry by adding a sufficient amount of ammonium hydroxide to said slurry to give a pH of about 8, filtering the hydrogel, washing the hydrogel, drying the hydrogel at about 125° C., calcining the dried hydrogel under flowing hydrogen at a temperature of about 500° C. for about 2 hours, then grinding the calcined product to yield particles of about 16 to about 60 mesh.

* * * * *